US00PP19765P2

(12) United States Plant Patent
Gutter

(10) Patent No.: US PP19,765 P2
(45) Date of Patent: Feb. 24, 2009

(54) ***LAVANDULA* PLANT NAMED 'LABLUSA'**

(50) Latin Name: *Lavandula angustifolia*
Varietal Denomination: Lablusa

(75) Inventor: Martien Everett Gutter, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/977,483

(22) Filed: Oct. 25, 2007

(51) Int. Cl.
*A01H 5/00* (2006.01)

(52) U.S. Cl. ..... Plt./445

(58) Field of Classification Search ..... Plt./445
See application file for complete search history.

*Primary Examiner*—Annette H Para
(74) *Attorney, Agent, or Firm*—S. Matthew Edwards

(57) ABSTRACT

A new *Lavandula* plant, particularly distinguished by its blue flower color, early flowering without cold induction, and compact plant habit.

1 Drawing Sheet

Latin name of the genus and species of the plant claimed: *Lavandula angustifolia.*
Varietal denomination: 'Lablusa'.

BACKGROUND OF THE NEW PLANT

The present invention comprises a new distinct cultivar of *Lavandula,* botanically known as *Lavandula angustifolia.*

The new *Lavandula* was not discovered but is a product of a planned breeding program conducted in Enkhuizen, Netherlands. The new *Lavandula* cultivar has a compact plant habit, a blue-purple flower color, and is early flowering.

The new *Lavandula* is propagated by cuttings resulting from a single seedling. This seedling from a selection in *Lavandula angustifolia* 'Hidcote Blue' (not patented, a seed strain), identified as number 'D804.' A plant was selected in this strain and the seeds of this plant were harvested in the field. The female parent is known and the male parent is a "cloud" of pollen of the other plants. These seeds were sown and the same cycle was done: in this population one plant was selected and harvested, so pollinated again with a "cloud" of pollen. A third cycle was done the same way and the final seedling was selected. This took place from June 1998 until July 2000 in Enkhuizen, Netherlands. The seedling was selected in July 2001 in Enkhuizen in field conditions.

The present cultivar has been repeatedly asexually reproduced by cuttings in Enkhuizen, Netherlands, since 2001. The distinctive characteristics of this new *Lavandula* are stable and reproduced true to type in successive generations of asexual reproduction.

The new *Lavandula* plant is a perennial in all climatic zones in the US.

DESCRIPTION OF THE DRAWING

The new *Lavandula* plant is illustrated by the accompanying photographic drawing which shows blooms, buds and foliage of the plant in full color, the color showing being as true as can be reasonably obtained by conventional photographic procedures.

BOTANICAL DESCRIPTION OF THE PLANT

The following detailed descriptions set forth the distinctive characteristics of this new *Lavandula.* The data which define these characteristics were collected from asexual reproductions carried out in Enkhuizen, the Netherlands. The plant history was taken on 15 week old plants. The instant plant was grown in an 11 cm container in an outdoor container field.

Color references are primarily to the R.H.S. Colour Chart of The Royal Horticultural Society of London.

Plants of the new *Lavandula* differ primarily from the plants of the originator 'Hidcote Blue' in the following characteristics:

Plants of the new *Lavandula* flower much earlier than plants of the originator 'Hidcote Blue.' Plants of the new *Lavandula* do not need cold for flower induction, whereas plants of the originator 'Hidcote Blue' need cold for flower induction. Flower heads of the new *Lavandula* are bigger and bluer than flower heads of the originator 'Hidcote Blue.'

TABLE 1

DIFFERENCES BETWEEN THE NEW CULTIVAR 'LABLUSA' AND A SIMILAR CULTIVAR

| | 'Lablusa' | 'Munstead' (Not patented) |
|---|---|---|
| Truss size | 3.4-4.3 cm | 2.2-2.8 cm |
| Leaf length | 4.3 cm | 3.4 cm |
| Time of flowering | 10-12 weeks after potting | 24-32 weeks after potting |

The plant:
*Classification.*—Botanical : *Lavandula angustifolia.*
Parentage:
*Originator selection.*—'Hidcote Blue' (Not patented).
Propagation:
*Type of cutting.*—Terminal cuttings.
*Time to initiate roots.*—12–14 days at 18° C.
*Time to produce a rooted cutting.*—3 weeks.
*Root description.*—Fine, fibrous and white in color.
Plant description:
*Shape.*—Globular, symmetrical.
*Height.*—39–45 cm.

*Diameter.*—24 cm.
*Vigor.*—Strong
*Branching habit.*—Freely branching.

The stem:
*Color.*—138A.
*Texture.*—Tender, pubescent.
*Length.*—18 cm.
*Diameter.*—2mm.
*Internode length.*—14 mm.
*Strength.*—Strong.
*Quantity.*—Appr. 50 per plant.

The foliage:
*Arrangement.*—Opposite, decussate.
*Number of leaves per stem.*—12.
*Leaf length.*—43 mm.
*Leaf width.*—5 mm.
*Shape of leaf.*—Ligulate.
*Shape of apex.*—Obtuse.
*Shape of base.*—Attenuate.
*Texture.*—Pubescent.
*Margin type.*—Entire.
*Fragrance.*—Present.
*Color.*—Upper surface : 137A. Lower surface : 137C.
*Petiole.*—Absent.
*Venation pattern.*—One central vein.

The flower:
*Natural flowering season.*—Summer.
*Flower type.*—Spike.
*Number of flowers per plant.*—250.
*Flower opening/closing behavior.*—Flowers stay open permanently.
*Fragrance.*—Strong.
*Spike height.*—5 cm.
*Spike diameter.*—2 cm.
*Bud* (*just before opening*).—Shape : Oval. Diameter : 4 mm. Length : 1 cm. Color : N88A.
*Corolla.*—Length upper lips : 3 mm. Length lower lips : 2 mm. Width upper lips : 3 mm. Width lower lips : 2 mm. Shape upper lips : Rounded with 2 bigger petals. Shape lower lips : Rounded with 3 smaller petals. Apex upper lips : Two lappets, incised. Apex lower lips : Three lappets, incised. Margin upper lips : Smooth, round. Margin lower lips : Smooth, round. Texture upper lips : Velvety. Texture lower lips : Velvety. Color when opening Upper lips (upper and lower surface) : N88B. Lower lips (upper and lower surface) : N88B. Color when fully opened Upper lips (upper and lower surface) : N88B. Lower lips (upper and lower surface) : N88B.
*Calyx.*—Arrangement : Tube, in spike. Sepal length : 5 mm. Sepal width : 2 mm. Shape : Oval and long. Texture : Pubescent. Color when opening : 86A. Color when fully opened : Top 86A, base 139D. Peduncle strength : Strong.
*Longevity of flowers.*—On the plant : Four weeks. Cut flowers : 12 hours.

Reproductive organs:
*Stamen.*—— Number per flower : 4. — Filament length : 1 mm.
*Anthers.*—Anther shape : Slender. Anther length : 2 mm. Anther color : 158D. Pollen color Greyed-Orange Group 164A.
*Pistil.*—Amount of pollen : Very small. Pistil length : 3 mm. Style length : 1 mm. Color : 158D. Stigma color 158D.

Disease resistance: No disease/pest resistance has been observed to date.

Weather tolerance: Heat tolerant to 42° C., susceptible to wet conditions.

Seed development: Seed development has not been observed to date.

What is claimed is:

1. A new and distinct cultivar of *Lavandula* plant named 'Lablusa,' as substantially illustrated and described herein.

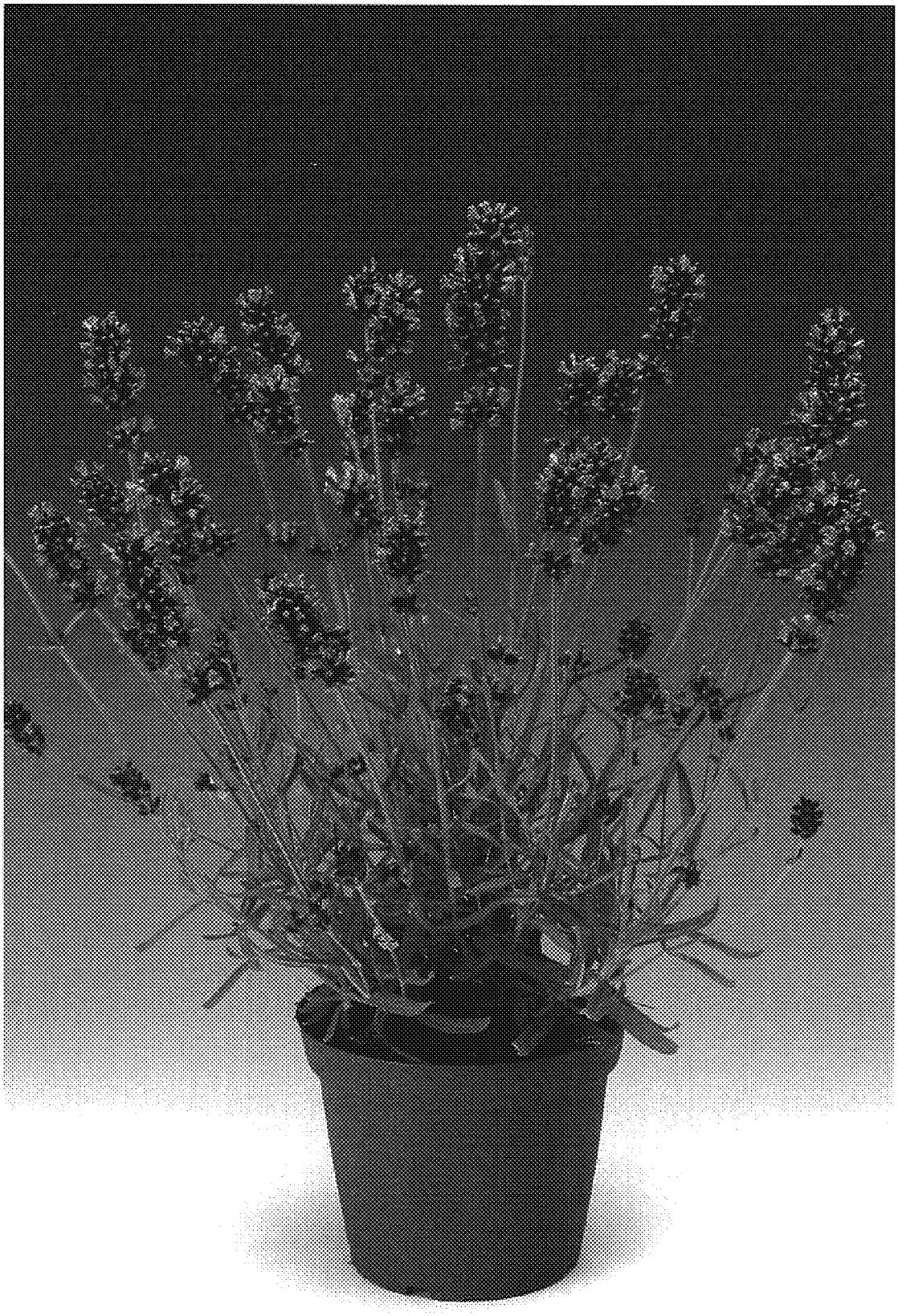

* * * * *